United States Patent
Gross et al.

(10) Patent No.: US 8,273,332 B2
(45) Date of Patent: *Sep. 25, 2012

(54) HAIR CARE PRODUCT CONTAINING ACETYLPYRIDINIUM SALTS

(75) Inventors: Wibke Gross, Hueckelhoven (DE);
Georg Knuebel, Duesseldorf (DE);
Thomas Mucha, Erkrath (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,727

(22) Filed: Nov. 15, 2011

(65) Prior Publication Data

US 2012/0058071 A1    Mar. 8, 2012

Related U.S. Application Data

(63) Continuation of application No. PCT/EP2010/054788, filed on Apr. 13, 2010.

(30) Foreign Application Priority Data

May 15, 2009    (DE) .................. 10 2009 003 155

(51) Int. Cl.
*A61Q 5/12*    (2006.01)
(52) U.S. Cl. ............ 424/70.1; 424/70.19; 424/70.21; 424/70.22
(58) Field of Classification Search ........ 424/70.1, 424/70.19, 70.21, 70.22
See application file for complete search history.

(56) References Cited

U.S. PATENT DOCUMENTS

| | | |
|---|---|---|
| 6,371,993 B1 | 4/2002 | Moeller et al. |
| 2011/0047712 A1* | 3/2011 | Gross et al. ............ 8/111 |

FOREIGN PATENT DOCUMENTS

| | | |
|---|---|---|
| DE | 102007047685 A1 | 7/2008 |
| WO | 9213829 A1 | 8/1992 |

* cited by examiner

*Primary Examiner* — Eisa Elhilo

(57) ABSTRACT

Cosmetic hair treatment agent comprising, in a cosmetically acceptable carrier, at least one surface-active agent chosen from cationic and/or zwitterionic surfactants, and at least one acetylpyridinium derivative of formula (I) for improving the general condition of the hair, for reducing hair damage in the interior of the hair, and for increasing the elasticity of hair.

13 Claims, No Drawings

HAIR CARE PRODUCT CONTAINING ACETYLPYRIDINIUM SALTS

CROSS REFERENCE TO RELATED APPLICATIONS

This application is a continuation of International Patent Application No. PCT/EP2010/054788 filed 13 Apr. 2010, which claims priority to German Patent Application No. 10 2009 003 155.3 filed 15 May 2009, both of which are incorporated herein by reference.

The present invention relates to conditioning and/or cleaning hair-treatment agents based on a special combination of an acetylpyridinium salt with a cationic and/or zwitterionic surfactant, and use of the agent for increasing hair-conditioning properties.

Today, human hair is treated with hair-cosmetic preparations in many different ways. These include cleaning of hair with shampoos, conditioning and regeneration with rinses and deep conditioners, as well as the bleaching, coloring and shaping of hair with colorants, tints, waving agents and styling preparations.

Due to the severe stressing of hair, for example, by coloring or permanent waves, by frequent cleaning of hair with shampoos and subsequent blow drying with hot air, by mechanical stresses, such as combing and styling, or by environmental stresses, such as sunlight, sea water or chlorinated water, the importance of care products with as long-lasting an action as possible is increasing. While consumers can minimize the degree of damage to their hair by reducing hair-cosmetic treatments, it is not possible to avoid environmental influences altogether. This means that hair can be damaged by stress, both externally and in its structure, giving it an unattractive appearance that can become noticeable as a lack of smoothness, softness and gloss, as well as poorer combability, hair breakage or split ends.

It has therefore been common for a long time to subject the hair to a special after-treatment which delivers care substances to the hair and scalp, imparting an attractive external appearance to the hair again and reinforce the hair structure as well as caring for the scalp and protecting it from drying out. In these after-treatments, the hair is treated with special active substances such as quaternary ammonium salts or special polymers, generally in the form of a rinse. As a result of this treatment, depending on the formulation, combability, hold, fullness and gloss of the hair can be improved and the rate of split ends reduced.

Still, it has been found that, as a result of coloring, permanent waves or blonding and subsequent washing and conditioning, the hair can perceptibly lose volume and fullness, so that cleaning and conditioning (which are necessary after a coloring, bleaching or permanent waving operation) also entail significant disadvantages for the aesthetics of the hair. Despite various efforts relating to hair care and regeneration in the last few decades, new problems in hair treatment are still appearing for which the experts have to work continuously on new solutions. The search for new ingredients with a positive effect on hair structure consequently remains highly topical. This invention disclosure therefore provides a novel agent for the care of hair having a structuring effect on hair fibers, making it possible to reverse damage already present in the hair as a "repair effect".

The present invention therefore provides cleaning and/or conditioning hair-treatment agents which do not have a negative effect on hair volume and hair fullness, particularly in previously colored, bleached and/or shaped hair. In particular, the present application provides agents for the regeneration of environmental influences, UV light irradiation, heat or special hair treatments.

There is a particular focus on providing an agent that develops a conditioning action not only by acting on the external layer of the hair (cuticle), but which is able to diffuse into the hair fibers, thereby strengthening the hair fibers over the entire cross section of the cortex.

To quantify hair damage or strengthening of hair fibers after a hair treatment, tensile properties of individual hair fibers are often determined. The stress-strain curves obtained here pass through three different regions, with it being possible to determine the modulus of elasticity (E modulus, Young's modulus) from tensile measurements in Hooke's range (up to 5% elongation) as a characteristic measured value.

Surface damage or abrasion damage, which affects the cuticle in particular, changes the tensile values only slightly. Active substances present in commercial deep conditioners and rinses are mainly cationic surfactants or polymers. These cationic compounds attach themselves to the outside of the cuticle by electrostatic interactions with the anionic groups of the hair. No structural improvement in the interior of the hair fibers can therefore be achieved with these care products.

Damage which negatively effects the structure of the cortex and strength of the hair results in reduced values of the modulus of elasticity. Substances that improve the strength of the hair structure lead to an increase in the modulus of elasticity. The determination of tensile values, particularly the modulus of elasticity, is therefore an ideal test method for identifying substances with a hair-structuring effect.

It has now been found that it is possible to achieve the above objects by providing hair-cleaning and/or conditioning agents which, in addition to a cationic and/or zwitterionic surfactant, contain at least one acetylpyridinium derivative in the form of an acetylpyridinium salt.

Acetylpyridinium derivatives according to the invention are already known from the literature as agents for producing coloring on hair (DE 19745356) or lightening hair (DE102007047685). There is no description in this context of the positive effects of the substances according to the invention on hair quality in hydrogen peroxide-free agents. It was not predictable, therefore, that the object according to the invention can be achieved by use of a combination of acetylpyridinium derivatives and certain surfactant systems.

The present invention therefore firstly provides a cosmetic hair-treatment agent containing, in a cosmetically acceptable carrier, a) at least one surface-active agent chosen from cationic and/or zwitterionic surfactants, and
b) at least one acetylpyridinium derivative of formula (I)—

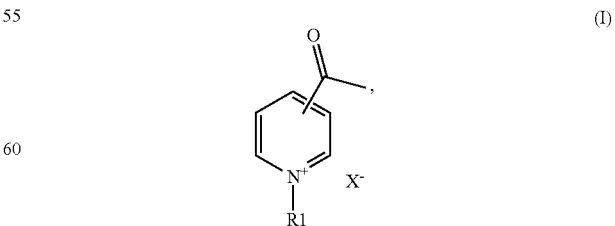

wherein R1 is a $C_1$-$C_6$ alkyl group, a $C_2$-$C_6$ alkenyl group, a $C_2$-$C_6$ hydroxyalkyl group, a $C_1$-$C_6$ alkoxy-$C_2$-$C_6$ alkyl group, a carboxy-$C_2$-$C_6$ alkyl group, an aryl-$C_1$-$C_6$ alkyl group, a heteroaryl-$C_1$-$C_6$ alkyl group, an aryl group or a heteroaryl group, and $X^-$ is a physiologically acceptable anion.

It has been shown that these agents are particularly capable in strengthening hair in the interior of its fibers and reducing structural damage. Overall, when the agent is used, a "repair effect" is observed.

The agents contain active substances in a cosmetic carrier. This cosmetic carrier is preferably aqueous, alcoholic or aqueous-alcoholic. Such carriers include creams, emulsions, gels or surfactant-containing foaming solutions, such as shampoos, foam aerosols or other preparations that are suitable for application to hair. An aqueous carrier contains, within the meaning of the invention, at least 40 wt. %, in particular at least 50 wt. %, water. Aqueous-alcoholic carriers within the meaning of the present invention are water-containing compositions containing 3 to 70 wt. % of a $C_1$-$C_4$ alcohol, in particular ethanol or isopropanol. The agents can additionally contain other organic solvents, such as methoxybutanol, ethyl diglycol, 1,2-propylene glycol, n-propanol, n-butanol, n-butylene glycol, glycerol, diethylene glycol monoethyl ether and diethylene glycol mono-n-butyl ether. All water-soluble organic solvents are preferred here.

Preferred agents additionally contain a non-aqueous solvent, with particularly preferred agents containing the solvent in a concentration of 0.1 to 30 wt. %, preferably in a concentration of 1 to 20 wt. % and most particularly preferably in a concentration of 2 to 10 wt. %, based on total agent.

As a first essential ingredient, the agents according to the invention contain an acetylpyridinium derivative according to formula (I). Examples of residues mentioned as substituents of the compounds of formula (I) are listed below:

Examples of $C_1$-$C_6$ alkyl residues include —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Examples of a $C_2$-$C_6$ alkenyl group are a prop-2-enyl group (allyl group), a 2-methylprop-2-enyl group, a but-3-enyl group, a but-2-enyl group, a pent-4-enyl group or a pent-3-enyl group, the prop-2-enyl group being preferred.

Examples of a $C_2$-$C_6$ hydroxyalkyl group include —$CH_2CH_2OH$, —$CH_2CH_2CH_2OH$, —$CH_2CH(OH)CH_3$ and —$CH_2CH_2CH_2CH_2OH$, with —$CH_2CH_2OH$ being preferred.

Examples of $C_1$-$C_6$ alkoxy-$C_2$-$C_6$ alkyl groups include —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, and —$CH_2CH_2CH_2OCH(CH_3)_2$.

Examples of a carboxy-$C_1$-$C_6$ alkyl group are carboxymethyl, 2-carboxyethyl and 3-carboxypropyl.

Examples of aryl-$C_1$-$C_6$ alkyl groups are the benzyl group and the 2-phenylethyl group.

Examples of a heteroaryl-$C_1$-$C_6$ alkyl group are the pyridin-2-yl methyl group, the pyridin-3-yl methyl group, the pyridin-4-yl methyl group, the pyrimidin-2-yl methyl group, the pyrrol-1-yl methyl group, the pyrrol-1-yl ethyl group, the pyrazol-1-yl methyl group or the pyrazol-1-yl ethyl group.

Examples of an aryl group are the phenyl group, the 1-naphthyl group or the 2-naphthyl group.

Examples of a heteroaryl group are pyridin-2-yl, pyridin-3-yl, pyridin-4-yl, pyrimidin-2-yl, pyrrol-1-yl, pyrrol-2-yl, pyrazol-1-yl, pyrazol-3-yl and pyrazol-2-yl.

In one embodiment, compounds according to formula (I) where R in the general structure (I) is a $C_1$-$C_6$ alkyl group, a $C_2$-$C_6$ alkenyl group or a $C_2$-$C_6$ hydroxyalkyl group are preferred.

It is particularly preferred according to the invention if R is a $C_1$-$C_6$ alkyl group, preferably methyl, ethyl, n-propyl or isopropyl and particularly preferably methyl.

It is preferred if the anion $X^-$ according to formula (I) is chosen from halide, in particular chloride, bromide and iodide, benzenesulfonate, p-toluenesulfonate, $C_1$-$C_4$ alkyl sulfonate, trifluoromethane sulfonate, acetate, trifluoroacetate, perchlorate, ½ sulfate, hydrogen sulfate, tetrafluoroborate, hexafluorophosphate or tetrachlorozincate. It is particularly favorable according to the invention if the physiologically acceptable anion $X^-$ is a halide ion (in particular chloride or bromide), hydrogen sulfate, ½ sulfate, p-toluenesulfonate, benzenesulfonate or acetate.

It has been shown that acetylpyridinium derivatives according to formula (I) have particularly advantageous properties if they carry the acetyl group in either the 2- or 4-position on the pyridine ring. In another embodiment, the agent contains as acetylpyridinium derivative according to formula (I) at least one 2-acetylpyridinium derivative and/or 4-acetylpyridinium derivative.

Suitable acetylpyridinium derivatives here are the physiologically acceptable salts which contain as cation an acetylpyridinium derivative chosen from 4-acetyl-1-methylpyridinium, 4-acetyl-1-allylpyridinium, 4-acetyl-1-(2-hydroxyethyl)pyridinium, 2-acetyl-1-methylpyridinium, 2-acetyl-1-allylpyridinium and 2-acetyl-1-(2-hydroxyethyl)pyridinium.

In particular, those agents wherein the acetylpyridinium derivative according to formula (I) is chosen from 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium chloride, 4-acetyl-1-methylpyridinium hydrogen sulfate, 4-acetyl-1-methylpyridinium acetate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium chloride, 4-acetyl-1-allylpyridinium hydrogen sulfate, 4-acetyl-1-allylpyridinium acetate, 2-acetyl-1-methylpyridinium p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogen sulfate and/or 2-acetyl-1-allylpyridinium acetate are suitable according to the invention.

Particularly advantageous agents are those wherein the acetylpyridinium derivative according to formula (I) is chosen from 4-acetyl-1-methylpyridinium p-toluenesulfonate and/or 2-acetyl-1-methylpyridinium p-toluenesulfonate, in particular 4-acetyl-1-methylpyridinium p-toluenesulfonate.

In one embodiment, the agents contain acetylpyridinium derivatives of formula (I) in an amount of 0.05 to 10 wt. %, preferably 0.1 to 7.5 wt. %, more preferably 0.2 to 6.5 wt. % and in particular 0.5 to 5 wt. %, based on total weight of the ready-to-use agent.

As another essential ingredient, agents according to the invention contain at least one surface-active agent chosen from cationic and/or zwitterionic surfactants.

According to another preferred embodiment, hair-treatment agents according to the invention are hair-conditioning agents based on cationic surfactants.

Depending on the desired treatment, the agent can be formulated as a shampoo, leave-in or rinse-off conditioner, deep conditioner, hair-conditioning spray emulsion or foam aerosol. It is generally a leave-on or rinse-off conditioner, deep conditioner, hair-conditioning spray emulsion or foam aerosol if the agent contains at least one cationic surfactant.

In another embodiment of the present invention, the agent is therefore formulated as a shampoo, leave-in or rinse-off conditioner, deep conditioner, hair-conditioning spray emulsion or foam aerosol.

Cationic surfactants are generally chosen from quaternary ammonium compounds and esterquats.

Preferred quaternary ammonium compounds are ammonium halides, in particular chlorides and bromides. In particular alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, behenyl trimethyl ammonium chloride, distearyl dimethyl ammonium chloride, lauryl dimethyl ammonium chloride, lauryl dimethyl benzyl ammonium chloride and tricetyl methyl ammonium chloride are suitable cationic surfactants according to the invention. Imidazolium compounds known under the INCI names Quaternium-27 and Quaternium-83 are also cationic surfactants that can be used according to the invention. The long alkyl chains of the above-mentioned surfactants preferably have 10 to 22 carbon atoms.

Esterquats are known substances having both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Products of this type are marketed, for example, under the trademarks Stepantex®, Dehyquart® and Armocare®. The products Armocare® VGH-70, an N,N-bis(2-palmitoyloxyethyl)dimethyl ammonium chloride, and Dehyquart® F-75, Dehyquart® C-4046, Dehyquart® L80 and Dehyquart® AU-35 are examples of these esterquats.

Use of cationic surfactants is not limited to hair-conditioning agents according to the invention. Indeed, hair-cleaning agents according to the invention can also contain cationic surfactants to increase skin compatibility and mildness.

The invention therefore also relates to those agents having, based on their total weight, 0.1 to 10 wt. %, preferably 0.15 to 7.5 wt. %, more preferably 0.2 to 6.5 wt. % and in particular 0.25 to 5 wt. % cationic surfactants.

Surface-active compounds having at least one quaternary ammonium group and at least one carboxylate, sulfonate or sulfate group in the molecule are referred to as zwitterionic surfactants. Particularly suitable zwitterionic surfactants are betaines such as N-alkyl-N,N-dimethyl ammonium glycinates, for example, cocoalkyl dimethyl ammonium glycinate, N-acylaminopropyl-N,N-dimethyl ammonium glycinates, for example, cocoacyl aminopropyl dimethyl ammonium glycinate, and 2-alkyl-3-carboxymethyl-3-hydroxyethyl imidazolines with 8 to 18 C atoms in the alkyl or acyl group in each case, and cocoacyl aminoethyl hydroxyethyl carboxymethyl glycinate. A preferred zwitterionic surfactant is the fatty acid amide derivative known under the INCI name Cocamidopropyl Betaine.

In another embodiment of the invention, the agent contains surface-active agents chosen from cationic and/or zwitterionic surfactants, in a total amount of 0.1 to 50 wt. %, preferably 0.5 to 25 wt. %, more preferably 1 to 20 wt. % and in particular 2 to 15 wt. %, based on total weight of the ready-to-use agent.

It is, furthermore, an aim of the present invention to provide the hair and scalp with skin- and hair-care substances on a lasting basis, without hair volume and hair fullness suffering as a result.

The above-mentioned active substances comprise at least one substance chosen from protein hydrolyzates, vitamins, amino acids, plant extracts and/or ectoine, present in the agents, based on total weight of the agent, in an amount of 0.001 to 10 wt. %, preferably in an amount of 0.01 to 7.5 wt. % and in particular in an amount of 0.1 to 5 wt. %.

In another embodiment, the agent therefore also contains at least one conditioning substance from the group of protein hydrolyzates and/or vitamins and/or amino acids and/or plant extracts and/or ectoine.

It may be preferred according to the invention that several substances from the above-mentioned group of active skin- and hair-care substances are present in the agent. A combination of at least one vitamin and at least one plant extract, an amino acid or ectoine or a combination of at least one protein hydrolyzate and at least one plant extract, an amino acid or ectoine, is preferred according to the invention. Particularly preferred is the combination of vitamins and amino acids, vitamins and ectoine, and protein hydrolyzates and amino acids.

Vitamins, provitamins and vitamin precursors, as well as derivatives thereof, that are preferred according to the invention are those representatives generally allocated to groups A, B, C, E, F and H.

Substances referred to as vitamin A include retinol (vitamin $A_1$) and 3,4-didehydroretinol (vitamin $A_2$). β-Carotene is the provitamin of retinol. Suitable vitamin A components include vitamin A acid and esters thereof, vitamin A aldehyde and vitamin A alcohol and esters thereof, such as palmitate and acetate. Agents according to the invention contain the vitamin A component preferably in amounts of 0.01 to 1 wt. %, based on total preparation.

The vitamin B group or vitamin B complex includes, inter alfa:

Vitamin $B_1$ (thiamin);

Vitamin $B_2$ (riboflavin);

Vitamin $B_3$, this name often including the compounds nicotinic acid and nicotinamide (niacinamide). Nicotinamide, which can be present in the agents preferably in amounts of 0.05 to 1 wt. %, based on total agent, is preferred according to the invention.

Vitamin $B_5$ (pantothenic acid and panthenol). In the context of this group, panthenol, in particular D-panthenol, is preferably used. Derivatives of panthenol that can be used according to the invention are, in particular, the esters and ethers of panthenol as well as cationically derivatized panthenols. Individual representatives include panthenol triacetate, panthenol monoethyl ether and the monoacetate thereof, as well as cationic panthenol derivatives disclosed in WO 92/13829.

Vitamin $B_6$ (pyridoxine as well as pyridoxamine and pyridoxal).

The above compounds of the vitamin B group are present in the agents preferably in amounts of 0.01 to 2 wt. %, based on total agent. Amounts of 0.03 to 1 wt. % are particularly preferred.

Vitamin C (ascorbic acid). Vitamin C is used in the agents preferably in amounts of 0.01 to 3 wt. %, based on total agent.

Use in the form of the palmitic ester, glucosides or phosphates may be preferred. Use in combination with tocopherols may likewise be preferred.

Vitamin E (tocopherols, particularly α-tocopherol). Tocopherol and its derivatives, including in particular esters such as acetate, nicotinate, phosphate and succinate, are present in the agents preferably in amounts of 0.01 to 1 wt. %, based on total agent.

Vitamin F. The term "vitamin F" is usually understood to mean essential fatty acids, in particular linoleic acid, linolenic acid and arachidonic acid.

Vitamin H. The compound (3aS,4S,6aR)-2-oxohexahydrothienol[3,4-d]-imidazole-4-valeric acid is referred to as vitamin H, but its trivial name biotin has now become accepted. Biotin is present in agents used according to the invention preferably in amounts of 0.0001 to 1.0 wt. %, in particular in amounts of 0.001 to 0.01 wt. %.

Agents according to the invention preferably contain vitamins, provitamins and vitamin precursors from the groups A, B, E and H. It is also possible for several vitamins and vitamin precursors to be present simultaneously. In a particularly preferred embodiment, the hair-treatment agents contain D-panthenol, optionally in a mixture with one of the other aforementioned vitamin components, to support moisture-retaining capacity of the scalp and/or hair.

Suitable protein hydrolyzates according to the invention are product mixtures obtained by acid-, base- or enzyme-catalyzed degradation of proteins. The term "protein hydrolyzates" according to the invention includes total hydrolyzates and individual amino acids and derivatives thereof, as well as mixtures of various amino acids. Polymers built up from amino acids and amino acid derivatives are also included under the term "protein hydrolyzates". The latter include, for example, polyalanine, polyasparagine, polyserine, etc. Other examples of useful compounds include L-alanyl-L-proline, polyglycine, glycyl-L-glutamine or D/L-methionine-S-methyl sulfonium chloride. It is also possible to use β-amino acids and derivatives thereof, such as β-alanine, anthranilic acid or hippuric acid. The molecular weight of protein hydrolyzates that can be used is from 75, the molecular weight of glycine, to 200,000. The molecular weight is preferably 75 to 50,000 and most particularly preferably 75 to 20,000 Daltons.

According to the invention, protein hydrolyzates of plant and animal, marine or synthetic origin can be used in an amount of 0.01 to 10 wt. %, preferably 0.05 to 5 wt. % and in particular 0.1 to 3 wt. %, based on total weight of the agent according to the invention.

Animal protein hydrolyzates include elastin, collagen, keratin, silk and milk protein hydrolyzates, which may also be present in the form of salts. These products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Kerasol® (Croda) or ProSina® (Croda).

Suitable protein hydrolyzates of vegetable origin include soy, almond, pea, potato, rice and wheat protein hydrolyzates. These products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although the use of the protein hydrolyzates as such is preferred, amino acid mixtures obtained otherwise can also be used in their place. Also possible is the use of derivatives of protein hydrolyzates, for example, in the form of their fatty acid condensation products. Such products are marketed, for example, under the names Lamepon® (Cognis), Lexein® (Inolex), Crolastin® (Croda) or Crotein® (Croda).

The addition of a keratin, collagen or silk protein hydrolyzate to the active substance combination according to the invention has proved particularly suitable. Keratin hydrolyzate is particularly preferred in relation to an increase in the moisture-retaining capacity.

As a further preferred active skin- and/or hair-care substance, agents according to the invention can contain, with particular preference, one or more amino acids. Amino acids also have a skin-moisturizing action and, owing to their buffer effect, stabilize the acid mantle of the skin (i.e., they are used for (scalp) skin protection). Suitable amino acids include glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cyss), L-carnitine, L-citrulline, L-theanine, 3',4'-dihydroxy-L-phenylalanine (L-dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, with it being possible to use both individual amino acids and mixtures.

Preferred agents contain one or more amino acids in relatively narrow ranges of quantities. Preferred hair-treatment agents contain, based on their weight, as care substance 0.01 to 5 wt. %, preferably 0.02 to 2.5 wt. %, particularly preferably 0.05 to 1.5 wt. %, more preferably 0.075 to 1 wt. % and in particular 0.1 to 0.25 wt. % amino acid(s), preferably from the group of glycine, alanine, arginine, serine, valine, lysine, leucine and/or threonine. Particularly preferred for use in the agents are the amino acids glycine, alanine and/or arginine.

As another preferred active skin and/or hair-care substance, agents according to the invention can particularly preferably contain plant extracts for mechanical and sensory strengthening of the hair.

These extracts are usually produced by extraction of the whole plant. In individual cases, however, it may also be preferred to produce the extracts exclusively from the flowers and/or leaves of the plant.

According to the invention, the extracts of green tea, oak bark, echinacea, stinging nettle, witch hazel, hops, henna, chamomile, burdock root, horsetail, whitethorn, lime-tree blossom, almond, aloe vera, pine needles, horse chestnut, sandalwood, juniper, coconut, mango, apricot, lime, wheat, kiwi, melon, orange, grapefruit, sage, rosemary, birch, mallow, cuckoo flower, wild thyme, yarrow, thyme, melissa, rest harrow, coltsfoot, marshmallow, meristem, moringa, ginseng and ginger root in particular are preferred.

Most particularly preferred due to their hair-strengthening action and their supporting action in relation to hair fullness are the extracts of green tea, chamomile, almond, aloe vera and moringa. According to the invention, a moringa extract is particularly preferred, for example, a product marketed with the trade name Puricare® LS 9658 or Moringa Oleifera®.

Plant extracts can be used according to the invention both in pure form and in dilute form. Where they are used in dilute form, they usually contain approx. 0.2-80 wt. % active substance and, as solvent, the extracting agent or mixture of extracting agents used to obtain them.

Furthermore, it may be preferred to use mixtures of more than one, in particular two, different plant extracts in agents according to the invention. Particularly preferred hair-treatment agents contain, based on their weight, 0.001 to 10 wt. %, preferably 0.005 to 5 and in particular 0.01 to 2 wt. %, plant extracts (corresponding to the active substance content of the extract).

As an additional active skin- and/or hair-care substance, agents according to the invention can also preferably contain ectoine ((4S)-2-methyl-1,4,5,6-tetrahydropyrimidine-4-carboxylic acid). Preferred hair-treatment agents contain, based on their weight, 0.001 to 10 wt. %, preferably 0.01 to 5 wt. %, particularly preferably 0.05 to 2.5 wt. % and in particular 0.1 to 1 wt. % (S)-2-methyl-1,4,5,6-tetrahydro-4-pyrimidine carboxylic acid (ectoine) as well as the physiologically acceptable salts of this compound and/or (S,S)-5-hydroxy-2-methyl-1,4,5,6-tetrahydro-4-pyrimidine carboxylic acid (hydroxyectoine) as well as the physiologically acceptable salts of this compound.

In another embodiment, the agent contains D-panthenol, keratin hydrolyzate, glycine, serine, arginine, Moringa oleifera extract and/or ectoine as an additional conditioning component.

In another embodiment, the hair-treatment agents also contain, based on their weight, in addition to the active substance combination according to the invention, a mixture of 0.01 to 2 wt. %, preferably 0.05 to 1.5 wt. % and in particular 0.1 to 1 wt. % D-panthenol and 0.01 to 2 wt. %, preferably 0.05 to 1.5 wt. % and in particular 0.1 to 1 wt. % glycine, serine and/or arginine.

In another embodiment of the invention, the hair-treatment agents also contain, based on their weight, in addition to the active substance combination according to the invention, a mixture of 0.01 to 2 wt. %, preferably 0.05 to 1.5 wt. % and in particular 0.1 to 1 wt. % D-panthenol and 0.01 to 2 wt. %, preferably 0.05 to 1.5 wt. % and in particular 0.1 to 1 wt. % ectoine.

In another embodiment of the invention, the hair-treatment agents also contain, based on their weight, in addition to the active substance combination according to the invention, a mixture of 0.01 to 2 wt. %, preferably 0.05 to 1.5 wt. % and in particular 0.1 to 1 wt. % D-panthenol and 0.01 to 2 wt. %, preferably 0.05 to 1.5 wt. % and in particular 0.1 to 1 wt. % moringa extract.

In another embodiment of the invention, to increase skin mildness and reduce skin irritation, the hair-treatment agents also contain at least one nonionic surfactant in an amount of 0.1 to 10 wt. %, preferably 0.15 to 7.5 wt. %, more preferably 0.2 to 6.5 wt. % and in particular 0.25 to 5 wt. %, based on total weight of the agent.

These nonionic surfactants include—
- addition products of 2 to 50 mol ethylene oxide and/or 0 to 5 mol propylene oxide to linear and branched fatty alcohols with 8 to 30 C atoms, to fatty acids with 8 to 30 C atoms and to alkyl phenols with 8 to 15 C atoms in the alkyl group;
- addition products of 2 to 50 mol ethylene oxide and/or 0 to 5 mol propylene oxide to linear and branched fatty alcohols with 8 to 30 C atoms, to fatty acids with 8 to 30 C atoms and to alkylphenols with 8 to 15 C atoms in the alkyl group, end-capped with a methyl or $C_2$-$C_6$ alkyl residue;
- $C_{12}$-$C_{30}$ fatty acid mono- and diesters of addition products of 1 to 30 mol ethylene oxide to glycerol;
- polyglycerol esters and alkoxylated polyglycerol esters;
- addition products of 5 to 60 mol ethylene oxide to optionally hydrogenated castor oil;
- alkoxylated, preferably propoxylated and in particular ethoxylated, mono-, di- and triglycerides, such as glycerol monolaurate +20 ethylene oxide and glycerol monostearate +20 ethylene oxide;
- alkoxylated fatty acid alkyl esters of the formula RC(O)—(OCH$_2$CH$_2$)$_w$OR', wherein RC(O)— is a linear or branched, saturated and/or unsaturated acyl residue with 6 to 22 carbon atoms, R' is linear or branched alkyl residues with 1 to 4 carbon atoms, and w is a number from 1 to 20;
- amine oxides;
- sorbitan fatty acid esters and addition products of ethylene oxide to sorbitan fatty acid esters, such as polysorbates, sorbitan monolaurate and sorbitan monolaurate +20 mol ethylene oxide (EO);
- sugar fatty acid esters and addition products of ethylene oxide to sugar fatty acid esters;
- addition products of ethylene oxide to fatty acid alkanolamides and fatty amines;
- fatty acid N-alkyl glucamides;
- alkylphenols and alkylphenol alkoxylates with 6 to 21, in particular 6 to 15, carbon atoms in the alkyl chain and 0 to 30 ethylene oxide and/or propylene oxide units; preferred representatives of this class include nonyiphenol +4 EO, nonyiphenol +9 EO, octylphenol +3 EO and octylphenol +8 EO; and
- alkyl polyglycosides corresponding to the general formula RO—(Z)$_x$, wherein R is alkyl, Z is sugar and x is the number of sugar units.

Suitable nonionic surfactants are in particular the alkylene oxide addition products to saturated linear fatty alcohols and fatty acids as well as $C_8$-$C_{22}$ alkyl mono- and oligoglycosides and ethoxylated analogs thereof. In particular the non-ethoxylated compounds have proved particularly suitable.

Particularly preferred are those alkyl polyglycosides of the formula RO—(Z)$_x$, wherein R consists of $C_8$-$C_{10}$ alkyl groups, of $C_{12}$-$C_{14}$ alkyl groups, substantially of $C_8$-$C_{16}$ alkyl groups, of $C_{12}$-$C_{16}$ alkyl groups or of $C_{16}$-$C_{18}$ alkyl groups. Alkyl polyglycosides that can be used according to the invention contain, on average, 1.1 to 5 sugar units. Alkyl polyglycosides with x values of 1.1 to 2.0 are preferred. Most particularly preferred are alkyl glycosides wherein x is 1.1 to 1.8.

In another embodiment, the hair-treatment agents also contain, in order to increase the cleaning efficiency of the agents, at least one anionic and/or amphoteric surfactant.

Suitable anionic surfactants in preparations according to the invention are all anionic surface-active substances suitable for use on the human body. These have an anionic group that imparts water-solubility, such as a carboxylate, sulfate, sulfonate or phosphate group, and a lipophilic alkyl group with about 8 to 30 C atoms. In addition, glycol or polyglycol ether groups, ester, ether and amide groups, as well as hydroxyl groups, can be present in the molecule. Examples of suitable anionic surfactants are, each in the form of their sodium, potassium and ammonium salts as well as mono-, di- and trialkanol ammonium salts with 2 to 4 C atoms in the alkanol group—
- linear and branched fatty acids with 8 to 30 C atoms (soaps),
- ether carboxylic acids of the formula RO(CH$_2$CH$_2$O)$_x$CH$_2$COOH, wherein R is a linear alkyl group with 8 to 30 C atoms and x=0 or 1 to 16,
- acyl sarcosides with 8 to 24 C atoms in the acyl group,
- acyl taurides with 8 to 24 C atoms in the acyl group,
- acyl isethionates with 8 to 24 C atoms in the acyl group,
- sulfosuccinic acid mono- and dialkyl esters with 8 to 24 C atoms in the alkyl group and sulfosuccinic acid monoalkyl polyoxyethyl esters with 8 to 24 C atoms in the alkyl group and 1 to 6 oxyethyl groups,
- linear alkane sulfonates with 8 to 24 C atoms,
- linear α-olefin sulfonates with 8 to 24 C atoms, sulfonates of unsaturated fatty acids with 8 to 24 C atoms and 1 to 6 double bonds, α-sulfo fatty acid methyl esters of fatty acids with 8 to 30 C atoms, alkyl sulfates and alkyl ether sulfates of the formula $RO(CH_2CH_2O)_xSO_3H$, wherein R is preferably a linear alkyl group with 8 to 30 C atoms and $x=0$ or 1 to 12, mixtures of surface-active hydroxy sulfonates, ether carboxylic acids of alkyl polyglycosides of the formula $R\text{-}(Gly)_xCH_2COOH$, wherein R is an alkyl group with 8 to 30 C atoms, Gly is a glycoside chosen from pyranosides, and x is a number from 1 to 5, sulfated hydroxyalkyl polyethylene and/or hydroxyalkylene propylene glycol ethers, esters of tartaric acid and citric acid with alcohols, which represent addition products of about 2-15 molecules of ethylene oxide and/or propylene oxide to fatty alcohols with 8 to 22 C atoms, alkyl and/or alkenyl ether phosphates of the formula

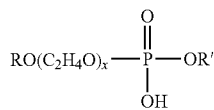

wherein R is preferably an aliphatic, optionally unsaturated hydrocarbon residue with 8 to 30 carbon atoms, R' is hydrogen or $(CH_2CH_2O)_yR$, and x and y, independently of one another, are a number from 1 to 10, sulfated fatty acid alkylene glycol esters of the formula $RC(O)O(alkO)_nSO_3H$, wherein R is a linear or branched, aliphatic, saturated and/or unsaturated alkyl residue with 6 to 22 C atoms, alk is $CH_2CH_2$, $CHCH_3CH_2$ and/or $CH_2CHCH_3$ and n is a number from 0.5 to 5, monoglyceride sulfates and monoglyceride ether sulfates of the formula (MGS)

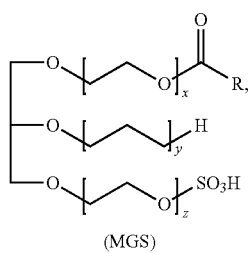

wherein R is a linear or branched alkyl residue with 6 to 22 carbon atoms and x, y and z in total is 0 or numbers from 1 to 30, preferably 2 to 10.

Preferred anionic surfactants for all hair-treatment agents according to the invention are linear and branched fatty acids with 8 to 30 C atoms, straight-chained and branched alkyl sulfates and alkyl polyglycol ether sulfates, ether carboxylic acids of the formula $RO(CH_2CH_2O)_x CH_2COOH$, wherein R is a linear alkyl group with 10 to 18 C atoms and $x=0$ or 1 to 12, and ether carboxylic acids of alkyl polyglycosides of the formula $R\text{-}(Gly)_xCH_2COOH$, wherein R is an alkyl group with 10 to 18 C atoms, Gly is a glycoside chosen from pyranosides, and x is a number from 1 to 5.

Amphoteric surfactants refer to surface-active compounds which, apart from a $C_8\text{-}C_{24}$ alkyl or acyl group, contain in the molecule at least one free amino group and at least one —COOH or —$SO_3H$ group and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkyl amidopropyl glycines, N-alkyltaurines, N-alkylsarcosines, 2-alkylaminopropionic acids and alkylaminoacetic acids with, in each case, about 8 to 24 C atoms in the alkyl group. Particularly preferred amphoteric surfactants are N-cocoalkyl aminopropionate, cocoacyl aminoethyl aminopropionate and $C_{12}\text{-}C_{18}$ acyl sarcosine.

Preferred agents contain anionic and/or amphoteric surfactants in a total amount of 0.1 to 30 wt. %, preferably from 0.5 to 20 wt. % and in particular from 1.0 to 15 wt. %, based on total weight of the agent.

In another preferred embodiment, the ready-to-use agent has a pH value from 2.0 to 9.0, preferably 2.5 to 7.0. Particularly preferred and especially skin-compatible are agents in a pH range from 3.0 to 6.0. The pH values within the meaning of the present invention are pH values measured at a temperature of 22° C.

The pH value is generally adjusted with pH regulators. To adjust the pH value, one skilled in the art is familiar with acidifying and alkalinizing agents that are common in cosmetics. Alkalinizing agents that can be used to adjust pH value are typically chosen from inorganic salts, in particular the alkali and alkaline earth metals, organic alkalinizing agents, in particular amines, basic amino acids and alkanolamines, and ammonia. Preferred acidifying agents according to the invention are food acids such as citric acid, acetic acid, malic acid or tartaric acid, as well as dilute mineral acids.

In addition to the compulsory components of the combination of active substances according to the invention, the hair-treatment agents according to the invention can, in a preferred embodiment, also contain additional hair-care substances, which can support or increase the action according to the invention still further.

These preferred additional active substances are chosen from natural and synthetic oil components, active anti-dandruff substances, cationic polymers, UV filters and/or silicones.

Cationic polymers can preferably be used according to the invention. Suitable cationic polymers according to the invention are polymers having in the main and/or side chain groups that can be "temporarily" or "permanently" cationic. According to the invention, those polymers which, independently of the pH value of the agent, have a cationic group, are referred to as "permanently cationic". These are generally polymers that contain a quaternary nitrogen atom, for example, in the form of an ammonium group. Preferred cationic groups are quaternary ammonium groups. In particular those polymers wherein the quaternary ammonium group is linked via a $C_{1\text{-}4}$ hydrocarbon group to a polymer main chain built up from acrylic acid, methacrylic acid or derivatives thereof, have proved particularly suitable.

A suitable homopolymer is the, optionally crosslinked, poly(methacryloyloxyethyl trimethyl ammonium chloride) with the INCI name Polyquaternium-37. Crosslinking may optionally take place with the aid of olefinically polyunsaturated compounds, for example, divinylbenzene, tetraallyl oxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose.

The homopolymer is preferably used in the form of a non-aqueous polymer dispersion having a polymer content of no less than 30 wt. %. Polymer dispersions of this type are commercially available under the names Salcare® SC 95 and Salcare® SC 96.

Copolymers with the above-mentioned cationic monomer units contain, as nonionogenic monomer units, preferably acrylamide, methacrylamide, acrylic acid $C_1$-$C_4$ alkyl esters and methacrylic acid $C_1$-$C_4$ alkyl esters. Among these nonionogenic monomers, acrylamide is particularly preferred. These copolymers can also be crosslinked, as in the case of the homopolymers described above. A preferred copolymer is the crosslinked acrylamide-methacryloyloxyethyl trimethyl ammonium chloride copolymer. Copolymers of this type are available commercially with the name Salcare® SC 92.

Other preferred cationic polymers include—
quaternized cellulose derivatives (e.g., Celquat® and Polymer JR®, preferably Celquat® H 100, Celquat® L 200 and Polymer JR®400),
hydrophobically modified cellulose derivatives (e.g., the commercial product SoftCat®),
cationic alkyl polyglycosides,
cationized honey (e.g., the commercial product Honeyquat® 50),
cationic guar derivatives (e.g., the commercial products Cosmedia® Guar and Jaguar®),
polysiloxanes with quaternary groups (e.g., the commercial products Q2-7224 (Dow Corning), Dow Corning® 929 Emulsion, SM-2059 (General Electric), SLM-55067 (Wacker) and Abil®-Quat 3270 and 3272 (Th. Goldschmidt; Quaternium-80)),
polymeric dimethyl diallyl ammonium salts and copolymers thereof (e.g., the commercial products Merquat®100 and Merquat®550),
copolymers of vinylpyrrolidinone with quaternized derivatives of dialkyl aminoalkyl acrylate and methacrylate (e.g., the commercial products Gafquat®734 and Gafquat®755),
vinylpyrrolidinone-vinylimidazolium methochloride copolymers (e.g., the commercial products Luviquat® FC 370, FC 550, FC 905 and HM 552),
quaternized polyvinyl alcohol, and
polymers known by the names Polyquaternium 2, Polyquaternium 17, Polyquaternium 18 and Polyquaternium 27 with quaternary nitrogen atoms in the main polymer chain.

It is also possible to use as cationic polymers polymers known by the names Polyquaternium-24 (commercial product, e.g. Quatrisoft® LM 200). Likewise, the copolymers of vinylpyrrolidinone, available as the commercial products Copolymer 845 (manufacturer: ISP), Gaffix® VC 713 (manufacturer: ISP), Gafquat®ASCP 1011, Gafquat®HS 110, Luviquat®8155 and Luviquat® MS 370, can be used according to the invention.

Other cationic polymers according to the invention are the "temporarily cationic" polymers. These polymers generally contain an amino group present at certain pH values as a quaternary ammonium group and thus in cationic form. For example, chitosan and derivatives thereof, freely available on the market, for example, with the trade names Hydagen® CMF, Hydagen® HCMF, Kytamer® PC and Chitolam® NB/101, are preferred.

In a particularly preferred embodiment of the invention, the agents also contain a cationic polymer for increasing the deposition of active cosmetic skin- and hair-care substances and for skin and hair conditioning. This is preferably a cationic guar derivative and/or Polyquaternium-7 (Merquat 550), Polyquaternium-6, Polyquaternium-10, Polyquaternium-67 (SoftCat® polymers) and or Salcare® SC 95 or Salcare® SC 96. The cationic polymer(s) is (are) used in agents according to the invention in an amount of 0.01 to 10 wt. %, preferably from 0.05 to 5 wt. % and in particular from 0.1 to 3 wt. %, based on the total weight of the agent.

Another preferred component according to the invention is an oil, which can be chosen from natural and synthetic oil components and/or fatty substances. In particular, conditioning agents according to the invention contain at least one oil and/or fat component.

As natural (vegetable) oils, triglycerides and mixtures of triglycerides are generally used. Preferred natural oils are coconut oil, (sweet) almond oil, walnut oil, peach kernel oil, apricot kernel oil, avocado oil, tea-tree oil, soybean oil, sesame oil, sunflower oil, tsubaki oil, evening primrose oil, rice bran oil, palm kernel oil, mango seed oil, cuckoo flower oil, thistle oil, macadamia nut oil, grape seed oil, amaranth seed oil, argan oil, bamboo oil, olive oil, wheat germ oil, pumpkin seed oil, mallow oil, hazelnut oil, safflower oil, canola oil, sasanqua oil, jojoba oil, cocoa butter and shea butter.

In particular, mineral oils, paraffin oils and isoparaffin oils as well as synthetic hydrocarbons are used as mineral oils. One hydrocarbon that can be used is, for example, 1,3-di-(2-ethylhexyl)cyclohexane (commercially available as Cetiol® S).

A dialkyl ether can also be used as the oil component. Dialkyl ethers that can be used according to the invention are, in particular, di-n-alkyl ethers with a total of 12 to 36 C atoms, in particular 12 to 24 C atoms, such as di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether as well as di-tert.-butyl ether, diisopentyl ether, di-3-ethyldecyl ether, tert.-butyl n-octyl ether, isopentyl n-octyl ether and 2-methylpentyl n-octyl ether. Particularly preferred according to the invention is di-n-octyl ether, commercially available under the name Cetiol® OE.

Agents according to the invention contain the oil component(s) preferably in an amount of 0.1 to 7 wt. %, in particular from 0.25 to 5 wt. %, based on total weight of the agent.

In another preferred embodiment, the action of the combination of active substances can be optimized still further by additional fatty substances. Additional fatty substances include fatty alcohols as well as natural and synthetic waxes, which can be present both in solid form and as a liquid in aqueous dispersion.

The amount of additional fatty substances used in this case is 0.1 to 15 wt. %, based on total agent. In a preferred embodiment, the amount is 0.5 to 10 wt. %, with amounts of 1 to 5 wt. % being most particularly advantageous.

Saturated, mono- or polyunsaturated, branched or unbranched fatty alcohols with $C_6$-$C_{30}$, preferably $C_{10}$-$C_{22}$ and particularly preferably $C_{12}$-$C_{22}$ carbon atoms can be used as fatty alcohols. According to the invention, it is possible to use, for example, decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well as Guerbet alcohols thereof, this list being exemplary and not limiting. The fatty alcohols preferably originate from natural fatty acids; however, it can usually be assumed that they are obtained from the esters of the fatty acids by reduction. It is likewise possible to use fatty alcohol blends produced by reduction of naturally occurring triglycerides, such as beef tallow, palm oil, ground-nut oil, rape seed oil, cotton seed oil, soybean oil, sunflower oil and flax oil or fatty acid esters obtained from transesterification products thereof with corresponding alcohols, and thus represent a mixture of different fatty alcohols. Such substances can be purchased, for example, with the names Stenol®, e.g. Stenol® 1618, or Lanette®, e.g. Lanette® 0, or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. It is also possible according to the invention to use wool wax alcohols, commercially available, for example, with the names Corona®, White Swan®, Coronet® or Fluilan®.

As natural or synthetic waxes, it is possible to use solid paraffins or isoparaffins, carnauba waxes, beeswaxes, candellila waxes, ozokerites, ceresin, sunflower wax, fruit waxes, such as for example apple wax or citrus wax, microwaxes of PE or PP. Waxes of this type are obtainable, for example, from Kahl & Co., Trittau.

Other fatty substances that can be used include— ester oils, which are the esters of $C_6$-$C_{30}$ fatty acids with $C_2$-$C_{30}$ fatty alcohols. Preferred are monoesters of fatty acids with alcohols having 2 to 24 C atoms. Particularly preferred are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoate (Cetiol® SN), decyl oleate (Cetiol® V); and dicarboxylic acid esters, such as di-n-butyl adipate, di-(2-ethylhexyl) adipate, di-(2-ethylhexyl) succinate and di-isotridecyl adipate as well as diol esters, such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate.

Anti-dandruff agents also contribute towards improving the agents, since the reduction or inhibition of dandruff is also associated with better skin compatibility and a lower irritation potential for the scalp. Preferred agents according to the invention therefore additionally contain at least one cosmetically acceptable active anti-dandruff substance. This is added to the compositions in an amount of 0.05 to 5 wt. %, preferably 0.1 to 3.0 wt. % and in particular 0.3 to 2.0 wt. % (based on total agent) and is chosen from piroctone olamine, climbazole, zinc pyrithione, ketoconazole, salicylic acid, sulfur, selenium sulfides, tar preparations, undecenoic acid derivatives, burdock root extracts, poplar extracts, stinging nettle extracts, walnut shell extracts, birch extracts, willow bark extracts, rosemary extracts and/or arnica extracts. Salicylic acid, climbazole, zinc pyrithione and piroctone olamine are preferred according to the invention.

Furthermore, in a preferred embodiment, an agent can also contain UV filters, since UV filters protect the scalp from the effects of elevated sun irradiation. In addition, it is known that certain active substances can cause skin irritation in combination with elevated sunlight or UV light irradiation, and it is therefore preferred if the agents additionally contain a UV filter. UV filters used according to the invention include substituted benzophenones, p-aminobenzoic acid esters, diphenyl acrylic acid esters, cinnamic acid esters, salicylic acid esters, benzimidazoles and o-aminobenzoic acid esters.

Examples of UV filters that can be used are 4-aminobenzoic acid, N,N,N-trimethyl-4-(2-oxoborn-3-ylidene methyl) aniline methyl sulfate, 3,3,5-trimethylcyclohexyl salicylate (homosalate), 2-hydroxy-4-methoxybenzophenone (benzophenone-3; Uvinul®M 40, Uvasorb® MET, Neo Heliopan®BB, Eusolex®4360), 2-phenylbenzimidazole-5-sulfonic acid and potassium, sodium and triethanolamine salts thereof (phenyl benzimidazole sulfonic acid; Parsol®HS; Neo Heliopan®Hydro), 3,3'-(1,4-phenylene dimethylene)bis(7,7-dimethyl-2-oxobicyclo-[2.2.1]hept-1-yl methanesulfonic acid) and salts thereof, 1-(4-tert.-butylphenyl)-3-(4-methoxyphenyl)propane-1,3-dione (butyl methoxydibenzoylmethane; Parsol®1789, Eusolex®9020), α-(2-oxoborn-3-ylidene)toluene-4-sulfonic acid and salts thereof, ethoxylated 4-aminobenzoic acid ethyl ester (PEG-25 PABA; Uvinul®P 25), 4-dimethyl aminobenzoic acid 2-ethylhexyl ester (octyl dimethyl PABA; Uvasorb®DMO, Escalol®507, Eusolex®6007), salicylic acid 2-ethylhexyl ester (octyl salicylate; Escalol®587, Neo Heliopan®OS, Uvinul®O18), 4-methoxycinnamic acid isopentyl ester (isoamyl p-methoxycinnamate; Neo Heliopan®E 1000), 4-methoxycinnamic acid 2-ethylhexyl ester (octyl methoxycinnamate; Parsol®MCX, Escalol®557, Neo Heliopan®AV), 2-hydroxy-4-methoxybenzophenone-5-sulfonic acid and its sodium salt (benzophenone-4; Uvinul®MS 40; Uvasorb®S 5), 3-(4'-methylbenzylidene)-D,L-camphor (4-methylbenzylidene camphor; Parsol®5000, Eusolex®6300), 3-benzylidene camphor (3-benzylidene camphor), 4-isopropyl benzyl salicylate, 2,4,6-trianilino-(p-carbo-2'-ethylhexyl-1'-oxy)-1,3,5-triazine, 3-imidazol-4-yl acrylic acid and ethyl esters thereof, polymers of N-{(2 and 4)-[2-oxoborn-3-ylidene methyl]benzyl}acrylamide, 2,4-dihydroxybenzophenone (benzophenone-1; Uvasorb®20 H, Uvinul®400), 1,1'-diphenylacrylonitrile acid 2-ethylhexyl ester (octocrylene; Eusolex®OCR, Neo Heliopan®Type 303, Uvinul®N 539 SG), o-aminobenzoic acid menthyl ester (menthyl anthranilate; Neo Heliopan®MA), 2,2',4,4'-tetrahydroxybenzophenone (benzophenone-2; Uvinul®D-50), 2,2'-dihydroxy-4,4'-dimethoxybenzophenone (benzophenone-6), 2,2'-dihydroxy-4,4'-dimethoxybenzophenone-5-sodium sulfonate and 2-cyano-3,3-diphenylacrylic acid 2'-ethylhexyl ester. 4-Aminobenzoic acid, N,N,N-trimethyl-4-(2-oxoborn-3-ylidene methyl)aniline methyl sulfate, 3,3,5-trimethylcyclohexyl salicylate, 2-hydroxy-4-methoxybenzophenone, 2-phenylbenzimidazole-5-sulfonic acid and potassium, sodium and triethanolamine salts thereof, 3,3'-(1,4-phenylene dimethylene)bis(7,7-dimethyl-2-oxobicyclo-[2.2.1]hept-1-yl methanesulfonic acid) and salts thereof, 1-(4-tert.-butylphenyl)-3-(4-methoxyphenyl)propane-1,3-dione, α-(2-oxoborn-3-ylidene) toluene-4-sulfonic acid and salts thereof, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and its sodium salt, 3-(4'-methylbenzylidene)-D,L-camphor, 3-benzylidene camphor, 4-isopropyl benzyl salicylate, 2,4,6-trianilino-(p-carbo-2'-ethylhexyl-1'-oxy)-1,3,5-triazine, 3-imidazol-4-yl acrylic acid and ethyl ester thereof, polymers of N-{(2 and 4)-[2-oxoborn-3-ylidene methyl] benzyl}acrylamide are preferred. 2-Hydroxy-4-methoxybenzophenone, 2-phenylbenzimidazole-5-sulfonic acid and its potassium, sodium and triethanolamine salts, 1-(4-tert.-butylphenyl)-3-(4-methoxyphenyl)propane-1,3-dione, 4-methoxycinnamic acid 2-ethylhexyl ester and 3-(4'-methylbenzylidene)-D,L-camphor are most particularly preferred.

Two preferred UV filters with cationic groups are cinnamic acid amidopropyl trimethyl ammonium chloride (Incroquat®UV-283) and dodecyl dimethylaminobenzamidopropyl dimethyl ammonium tosylate (Escalol® HP 610), available commercially.

UV filters are present in agents according to the invention generally in amounts of 0.1 to 5 wt. %, preferably 0.4 to 2.5 wt. %, based on total agent.

Particularly preferred are hair-treatment agents according to the invention having at least one silicone. Silicones bring about excellent conditioning properties on the hair. In particular, they bring about better combability of the hair in the wet and dry state and in many cases have a positive effect on the handle and softness of the hair.

It is therefore desirable according to the invention to add at least one silicone component, particularly in the case of hair conditioning agents. This is/these are chosen from:
i) polyalkyl siloxanes, polyaryl siloxanes, polyalkyl aryl siloxanes, which are volatile or non-volatile, straight-chained, branched or cyclic, crosslinked or uncrosslinked;
ii) polysiloxanes containing in their general structure one or more organofunctional groups, which are chosen from substituted or unsubstituted aminated groups; (per)fluorinated groups; thiol groups; carboxylate groups; hydroxylated groups; alkoxylated groups; acyloxy alkyl groups; amphoteric groups; sulfinic acid groups; hydroxyacylamino groups; carboxy groups; sulfonic acid groups; and sulfate or thiosulfate groups;
iii) linear polysiloxane (A)-polyoxyalkylene (B) block copolymers;
iv) grafted silicone polymers with a non-silicone-containing, organic basic framework;
v) grafted silicone polymers with a polysiloxane basic framework;
vi) or mixtures thereof.

The above-mentioned silicone components are added to the agents, based on total weight of the agent, in an amount of 0.1 to 10 wt. %, preferably 0.2 to 7.5 wt. % and in particular 0.3 to 5 wt. % (based on the active substance content of silicone).

In another preferred embodiment, the agents can contain emulsifiers. Emulsifiers cause formation of water- or oil-stable adsorption layers at the phase interface, which protect the dispersed droplets from coalescence and thus stabilize the emulsion. Emulsifiers, like surfactants, are therefore constructed from a hydrophobic molecular moiety and a hydrophilic molecular moiety. Hydrophilic emulsifiers preferentially form O/W emulsions and hydrophobic emulsifiers preferentially form W/O emulsions. An emulsion refers to a droplet-like distribution (dispersion) of one liquid in another liquid with an expenditure of energy to create stabilizing phase interfaces by surfactants. Choice of these emulsifying surfactants or emulsifiers is governed by the substances to be dispersed and the particular outer phase, and also the finely divided nature of the emulsion. Useful emulsifiers according to the invention include—
addition products of 4 to 30 mol of ethylene oxide and/or 0 to 5 mol of propylene oxide onto linear fatty alcohols having 8 to 22 C atoms, onto fatty acids having 12 to 22 C atoms and onto alkylphenols having 8 to 15 C atoms in the alkyl group;
$C_{12}$-$C_{22}$ fatty acid mono- and diesters of addition products of 1 to 30 mol of ethylene oxide onto polyols having 3 to 6 carbon atoms, in particular, onto glycerol;
ethylene oxide and polyglycerol addition products onto methyl glucoside fatty acid esters, fatty acid alkanolamides and fatty acid glucamides,
$C_8$-$C_{22}$ alkyl mono- and oligoglycosides and ethoxylated analogs thereof, where degrees of oligomerization of from 1.1 to 5, in particular 1.2 to 2.0, and glucose as sugar component are preferred;
mixtures of alkyl (oligo)glucosides and fatty alcohols, (e.g., commercially available as Montanov®68);
addition products of 5 to 60 mol of ethylene oxide onto optionally hydrogenated castor oil;
partial esters of polyols having 3-6 carbon atoms with saturated $C_8$-$C_{22}$ fatty acids;
sterols, in particular of animal origin (zoosterols, e.g., cholesterol and lanosterol) and also of plant origin (phytosterols, e.g., ergosterol, stigmasterol and sitosterol), as well as from fungi and yeasts (mycosterols);
phospholipids, in particular glucose phospholipids (e.g., as lecithins or phosphatidylcholines from e.g. egg yolk or plant seeds (e.g., soybeans);
fatty acid esters of sugars and sugar alcohols, such as sorbitol; and
polyglycerols and polyglycerol derivatives.

Agents according to the invention contain emulsifiers preferably in amounts of 0.1-25 wt. %, in particular 0.5-15 wt. %, based on total agent.

Compositions according to the invention can preferably contain at least one nonionogenic emulsifier with an HLB value of 8 to 18. Nonionogenic emulsifiers with an HLB value of 10 to 15 may be particularly preferred.

Furthermore, the agents can contain other active substances, auxiliary substances and additives, in particular—
nonionic polymers such as vinylpyrrolidinone/vinyl acrylate copolymers, polyvinylpyrrolidinone and vinylpyrrolidinone/vinyl acetate copolymers and polysiloxanes;
zwitterionic and amphoteric polymers such as acrylamidopropyl trimethyl ammonium chloride/acrylate copolymers and octylacrylamide/methyl methacrylate/tert.-butyl aminoethyl methacrylate/2-hydroxypropyl methacrylate copolymers;
anionic polymers such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl-acrylamide terpolymers;
thickeners such as agar-agar, guar gum, alginates, xanthan gum, gum arabic, karaya gum, locust bean gum, flaxseed gum, dextrans, cellulose derivatives (e.g., methyl cellulose, hydroxyalkyl cellulose and carboxymethyl cellulose), starch fractions and derivatives such as amylose, amylopectin and dextrins, clays such as bentonite, or fully synthetic hydrocolloids such as polyvinyl alcohol;
structurants such as glucose, maleic acid and lactic acid;
perfume oils, dimethyl isosorbide and cyclodextrins;
fiber-structure improving active substances, particularly mono-, di- and oligosaccharides such as glucose, galactose, fructose, fruit sugar and lactose;
dyes and pigments for coloring the agent;
complexing agents such as EDTA, NTA, β-alanine diacetic acid and phosphonic acids;
swelling and penetrating substances such as glycerol, propylene glycol monoethyl ether, carbonates, hydrogen carbonates, guanidines, ureas and primary, secondary and tertiary phosphates;

opacifiers such as latex, styrene/PVP and styrene/acrylamide copolymers;

pearlescent agents such as ethylene glycol mono- and distearate and PEG-3 distearate;

propellants such as propane-butane mixtures, $N_2O$, dimethyl ether, $CO_2$ and air; and antioxidants.

One skilled in the art chooses these additional substances according to the desired properties of the agents.

The present invention secondly provides for use of a hair-treatment agent comprising, in a cosmetic carrier, at least one acetylpyridinium derivative of formula (I)—

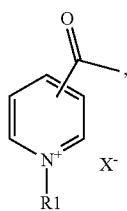
(I)

wherein R1 is a $C_1$-$C_6$ alkyl group, a $C_2$-$C_6$ alkenyl group, a $C_2$-$C_6$ hydroxyalkyl group, a $C_1$-$C_6$ alkoxy-$C_2$-$C_6$ alkyl group, a carboxy-$C_2$-$C_6$ alkyl group, an aryl-$C_1$-$C_6$ alkyl group, a heteroaryl-$C_1$-$C_6$ alkyl group, an aryl group or a heteroaryl group; and $X^-$ is a physiologically acceptable anion for reducing hair damage in the interior of the hair and for increasing the elasticity of the hair.

One embodiment of this subject-matter of the invention is use of a hair-treatment agent according to the second subject-matter of the invention for restructuring the hair cortex.

Another embodiment of this subject-matter of the invention is use of a hair-treatment agent according to the second subject-matter of the invention for improving the condition of hair.

In one embodiment, the hair-treatment agent additionally contains at least one surface-active agent chosen from cationic and/or zwitterionic surfactants.

With regard to further embodiments of uses according to the invention, the statements regarding the agents according to the invention apply *mutatis mutandis*.

The following examples explain the invention without limiting it thereto.

EXAMPLES

1. Tensile Measurements on Damaged and Undamaged Hair

For each series of measurements, 50 individual hairs (Alkinco, natural dark European hair) were chosen. For the measurement on damaged hair, the hair was deliberately damaged by two applications of a permanent wave (cold wave). The diameter of each hair was then determined using a laser scan micrometer at a temperature of 22° C. and a relative humidity of 50%. Then, the hair was extended using a tensile tester (Diastron Ltd.) in the elastic range, and the modulus of elasticity was calculated.

The hair was then treated three times in succession with a 1% solution of 4-acetyl-1-methylpyridinium p-toluenesulfonate in water. The solution of the active substance was allowed to act on each individual hair for 30 minutes in each case and then rinsed out for 90 seconds.

After this application, the hair was again extended using a tensile tester (Diastron Ltd.) in the elastic range. The modulus of elasticity was calculated again. Individual values from each series of measurements were statistically evaluated. A positive percentage change in the modulus of elasticity means that, following application of the conditioning substance, more force is needed to deform the hair by a specific amount within the elastic range. This is an indicator of strengthening of the hair structure.

It was found that when the 4-acetyl-1-methylpyridinium p-toluenesulfonate solution is applied to undamaged hair, the modulus of elasticity is increased by 1%. When it is applied to damaged hair, the percentage increase in the modulus of elasticity even rises statistically significantly by 2.2%. Thus, proof of the structuring effect of the active substance is provided.

2. Formulations (All Data are in Percent by Weight Unless Otherwise Specified)

Hair-Care Shampoo 1:

| | |
|---|---|
| Ethoxylated fatty alcohol sulfate ($C_{12}$-$C_{14}$, 2 EO; 70% AS) | 15.0 |
| Disodium cocoamphodiacetate | 7.0 |
| Euperlan ® PK 3000 AM [1] | 2.5 |
| Coconut glycerides + 7.3 EO | 0.5 |
| Cutina HR ® [2] | 0.1 |
| D-Panthenol | 0.5 |
| 4-Acetyl-1-methylpyridinium p-toluenesulfonate [3] | 0.5 |
| Citric acid | 0.5 |
| Salicylic acid | 0.2 |
| Glycerol | 0.15 |
| Sodium benzoate | 0.4 |
| NaCl | 1.0 |
| Perfume | qs |
| Water | to 100 |

Hair-Care Shampoo 2:

| | |
|---|---|
| Ethoxylated fatty alcohol sulfate ($C_{12}$-$C_{14}$, 2 EO; 70% AS) | 15.0 |
| Cocamidopropyl betaine | 5.0 |
| Plantacare ® [4] 818 UP | 4.0 |
| Coconut glycerides + 7.3 EO | 0.5 |
| D-Panthenol | 0.5 |
| Glycine | 0.2 |
| 4-Acetyl-1-methylpyridinium p-toluenesulfonate | 0.3 |
| Citric acid | 0.5 |
| Sodium benzoate | 0.4 |
| Glycerol | 0.1 |
| NaCl | 1.0 |
| Perfume | qs |
| Water | to 100 |

Hair-Care Shampoo 3:

| | |
|---|---|
| Ethoxylated fatty alcohol sulfate ($C_{12}$-$C_{14}$, 2 EO; 70% AS) | 15.0 |
| Cocamidopropyl betaine | 2.0 |
| Disodium cocoamphodiacetate | 3.0 |
| Plantacare ® [4] 818 UP | 4.0 |
| Coconut glycerides + 7.3 EO | 0.5 |
| ProSina ® [5] | 0.5 |
| 4-Acetyl-1-methylpyridinium p-toluenesulfonate | 0.75 |
| Citric acid | 0.5 |
| Sodium benzoate | 0.4 |
| Mannitol | 0.1 |
| NaCl | 1.0 |
| Perfume | qs |
| Water | to 100 |

Hair-Care Shampoo 4:

| | |
|---|---|
| Ethoxylated fatty alcohol sulfate ($C_{12}$-$C_{14}$, 2 EO; 70% AS) | 15.0 |
| Cocamidopropyl betaine | 5.0 |
| Plantacare ® [4] 818 UP | 4.0 |
| Coconut glycerides + 7.3 EO | 0.5 |
| D-Panthenol | 0.5 |
| Ectoine | 0.2 |
| 4-Acetyl-1-methylpyridinium p-toluenesulfonate | 0.5 |
| Citric acid | 0.5 |
| Sodium benzoate | 0.4 |
| Sorbitol | 0.1 |
| NaCl | 1.0 |
| Perfume | qs |
| Water | to 100 |

Lightening Hair-Care Shampoo 5:

| | |
|---|---|
| Ethoxylated fatty alcohol sulfate ($C_{12}$-$C_{14}$, 2 EO; 70% AS) | 15.0 |
| Disodium cocoamphodiacetate | 7.0 |
| Euperlan ® PK 3000 AM [1] | 2.5 |
| Coconut glycerides + 7.3 EO | 0.5 |
| Cutina HR ® [2] | 0.1 |
| D-Panthenol | 0.5 |
| 4-Acetyl-1-methylpyridinium p-toluenesulfonate | 0.5 |
| Citric acid | 0.5 |
| Hydrogen peroxide | 0.2 |
| Salicylic acid | 0.2 |
| Trisodium citrate dihydrate | 0.2 |
| Sodium benzoate | 0.4 |
| Glycerol | 0.2 |
| NaCl | 1.0 |
| Perfume | qs |
| Water | to 100 |

Rinse-Off Conditioner I:

| | |
|---|---|
| Cetearyl Alcohol | 2.5 |
| Eumulgin ® B2 [6] | 0.5 |
| Genamin KDMP ® [7] | 3.0 |
| Cutina CP ® [8] | 0.5 |
| Natrosol 250 HR ® [9] | 0.5 |
| Timiron Super Silver ® [10] | 0.1 |
| Mannitol | 0.1 |
| Glycine | 0.2 |
| Methyl paraben | 0.3 |
| Phenoxyethanol | 0.4 |
| D-Panthenol | 0.5 |
| 4-Acetyl-1-methylpyridinium p-toluenesulfonate | 1.0 |
| Perfume | qs |
| Water | to 100 |

A rinse-off conditioner II with a lightening effect additionally contains 0.4 wt. % hydrogen peroxide and 0.2 wt. % citric acid.

Leave-On Conditioner III: Spray Emulsion:

| | |
|---|---|
| Ethanol 96% DEP denatured | 10.0 |
| Dow Corning 5330 Fluid ® [1] | 2.0 |
| Dow Corning 949 ® [12] | 5.0 |
| PEG-40 hydrogenated castor oil | 1.0 |
| Sodium benzoate | 0.1 |
| Sorbitol | 0.1 |
| ProSina ® [5] | 0.2 |
| 4-Acetyl-1-methylpyridinium p-toluenesulfonate | 1.0 |
| Perfume | qs |
| Water | to 100 |

A leave-on-conditioner IV with a lightening effect additionally contains 0.1 wt. % hydrogen peroxide and 0.4 wt. % citric acid.

Leave-On-Conditioner V (Foam Aerosol):

| | |
|---|---|
| Salcare ® [13] SC 96 | 2.0 |
| Genamin ® [14] CTAC | 1.5 |
| Dow Corning ® [15] 939 | 0.5 |
| D-Panthenol | 0.2 |
| Glycine | 0.1 |
| 4-Acetyl-1-methylpyridinium p-toluenesulfonate | 0.5 |
| Methylparaben | 0.2 |
| Phenoxyethanol | 0.4 |
| Glycerol | 0.15 |
| Isobutane | 6.0 |
| Perfume | qs |
| Water | to 100 |

A leave-on-conditioner VI with a lightening effect additionally contains 0.2 wt. % hydrogen peroxide and 0.3 wt. % citric acid.

The following commercial products were used:
1 INCI name: Aqua, Glycol Distearate, Glycerin, Laureth-4, Cocamidopropyl Betaine, Formic Acid (Solids: 41-45%); Cognis
2 INCI name: Hydrogenated Castor Oil; Cognis
3 For the production of 4-acetyl-1-methylpyridinium p-toluenesulfonate, cf. Offenlegungsschrift DE 102007047685 A1
4 INCI name: Coco-Glucoside (AS 51-53%); Cognis
5 INCI name: Aqua, Hydrolyzed Keratin; Croda
6 INCI name: Ceteareth-20; Cognis
7 INCI name: Behentrimonium Chloride; Cognis
8 INCI name: Cetyl Palmitate; Cognis
9 INCI name: Hydroxyethylcellulose; Hercules
10 INCI name: Mica; Cl 77891; Merck
11 INCI name: PEG/PPG-15/15-Dimethicone; Dow Corning
12 INCI name: Amodimethicone, Cetrimonium Chloride, Trideceth-12; Dow Corning
13 INCI name: Polyquaternium-37, Propylene Glycol, Dicaprylate/Dicaprate, PPG-1 Trideceth-6; Ciba
14 INCI name: Cetrimonium Chloride; Cognis
15 INCI name: Amodimethicone, Cetrimonium Chloride, Trideceth-12; Dow Corning

We claim:
1. Cosmetic hair-treatment agent comprising, in a cosmetically acceptable carrier:
at least one surface-active agent chosen from cationic and/or zwitterionic surfactants;
at least one acetylpyridinium derivative of formula (I),

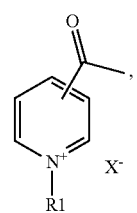

wherein R1 is a $C_1$-$C_6$ alkyl group, a $C_2$-$C_6$ alkenyl group, a $C_2$-$C_6$ hydroxyalkyl group, a $C_1$-$C_6$ alkoxy-$C_2$-$C_6$ alkyl group, a carboxy-$C_2$-$C_6$ alkyl group, an aryl-$C_1$-$C_6$ alkyl group, a heteroaryl-$C_1$-$C_6$ alkyl group, an aryl group or a heteroaryl group; and X⁻ is a physiologically acceptable anion and at least one conditioning substance chosen from, vitamins, amino acids, plant extracts and/or ectoine.

2. Agent according to claim 1, wherein R1 is a $C_1$-$C_6$ alkyl group, a $C_2$-$C_6$ alkenyl group or a $C_2$-$C_6$ hydroxyalkyl group.

3. Agent according to claim 1, wherein the at least one acetylpyridinium derivative is at least a 2-acetylpyridinium derivative and/or 4-acetylpyridinium derivative.

4. Agent according to claim 1, wherein the acetylpyridinium derivative according to formula (I) is chosen from 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium chloride, 4-acetyl-1-methylpyridinium hydrogen sulfate, 4-acetyl-1-methylpyridinium acetate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium chloride, 4-acetyl-1-allylpyridinium hydrogen sulfate, 4-acetyl-1-allylpyridinium acetate, 2-acetyl-1-methylpyridinium p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogen sulfate and/or 2-acetyl-1-allylpyridinium acetate.

5. Agent according to claim 4, wherein the acetylpyridinium derivative according to formula (I) is chosen from 4-acetyl-1-methylpyridinium p-toluenesulfonate and/or 2-acetyl-1-methylpyridinium p-toluenesulfonate.

6. Agent according to claim 1 comprising 0.05 to 10 wt. % of the acetylpyridinium derivative according to formula (I), based on total weight of the agent.

7. Agent according to claim 1, wherein the at least one surface-active agent is at least a cationic surfactant.

8. Agent according to claim 1, comprising 0.1 to 50 wt. % of the at least one surface-active agent, based on total weight of the agent.

9. Agent according to claim 1, wherein the at least one conditioning substance is D-panthenol, glycine, serine, arginine and/or Moringa oleifera extract.

10. Shampoo, leave-in or rinse-off conditioner, deep conditioner, hair-conditioning spray emulsion or foam aerosol comprising the agent according to claim 1.

11. Method of reducing hair damage in the interior of the hair and increasing elasticity of the hair comprising applying to the hair a hair-treatment agent comprising, in a cosmetically acceptable carrier, at least one acetylpyridinium derivative of formula (I)—

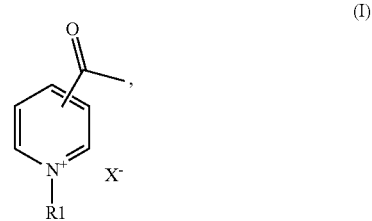

wherein R1 is a $C_1$-$C_6$ alkyl group, a $C_2$-$C_6$ alkenyl group, a $C_2$-$C_6$ hydroxyalkyl group, a $C_1$-$C_6$ alkoxy-$C_2$-$C_6$ alkyl group, a carboxy-$C_2$-$C_6$ alkyl group, an aryl-$C_1$-$C_6$ alkyl group, a heteroaryl-$C_1$-$C_6$ alkyl group, an aryl group or a heteroaryl group; and X⁻ is a physiologically acceptable anion and at least one conditioning substance chosen from, vitamins, amino acids, plant extracts and/or ectoine.

12. Method of restructuring hair cortex comprising applying an agent according to claim 1 onto the hair.

13. Method of improving the condition of hair comprising applying an agent according to claim 1 onto the hair.

* * * * *